United States Patent [19]
Roche

[11] Patent Number: 5,520,667
[45] Date of Patent: May 28, 1996

[54] METHODS FOR BONE AND OTHER TISSUE PREPARATION

[75] Inventor: Karen M. Roche, Stillwater, Minn.

[73] Assignee: Innovative Surgical Devices Corporation, Stillwater, Minn.

[21] Appl. No.: 268,297

[22] Filed: Jun. 29, 1994

[51] Int. Cl.$^6$ .................................................. A61M 35/00
[52] U.S. Cl. ........................................... 604/290; 128/750
[58] Field of Search ......................... 128/200.14, 200.19, 128/200.21, 200.22, 749, 750, 897, 898; 604/23, 24, 26, 27, 28, 49, 56, 118, 121, 123, 289, 290, 902; 433/98, 99, 100, 216

[56] References Cited

U.S. PATENT DOCUMENTS

| | | |
|---|---|---|
| 2,812,765 | 11/1957 | Tofflemire . |
| 3,085,573 | 4/1963 | Meyer et al. . |
| 3,353,537 | 11/1967 | Knox et al. . |
| 3,561,433 | 2/1971 | Kovach . |
| 4,007,739 | 2/1977 | Bron et al. . |
| 4,215,476 | 8/1980 | Armstrong . |
| 4,299,221 | 11/1981 | Phillips et al. . |
| 4,519,385 | 5/1985 | Atkinson et al. . |
| 4,526,573 | 7/1985 | Lester et al. . |
| 4,583,531 | 4/1986 | Mattchen . |
| 4,655,197 | 4/1987 | Atkinson . |
| 4,662,829 | 5/1987 | Nehring . |
| 5,037,437 | 8/1991 | Matsen, III . |
| 5,046,486 | 9/1991 | Grulke et al. . |

OTHER PUBLICATIONS

*CarboJet*™ *Bone Lavage System* brochure, Innovative Surgical Devices Corporation, Stillwater, Minnesota, 2 pages.
*Pulsatile Irrigation in Orthopedics*, Pulsatile Irrigation, Sobel and Goldberg, Aug. 1985, vol. 8, No. 8, pp. 1019–1022.

*Primary Examiner*—C. Fred Rosenbaum
*Assistant Examiner*—Bryan L. Tsosie
*Attorney, Agent, or Firm*—Merchant, Gould, Smith, Edell, Welter & Schmidt

[57] ABSTRACT

Methods are provided for surgical lavage including pumping liquid to bone and other tissue surfaces with a reciprocating pump mechanism operated by pressurized gas wherein pressurized exhaust gas is further utilized to accelerate the pulsed liquid. A first valve arrangement is provided to bypass the pumping mechanism to direct pressurized gas directly onto the tissue surface without the presence of liquid from the device. A second valve arrangement is provided for optionally venting at least a portion of the exhaust gas to the atmosphere instead of directing it to the tissue surface. An additive line delivers additive to the gas bypass line for delivery of the additive to the tissue surface with the flowing gas stream.

6 Claims, 10 Drawing Sheets

METHODS FOR BONE AND OTHER TISSUE PREPARATION

FIELD OF THE INVENTION

The invention relates generally to hand-held surgical lavage devices and methods, and more particularly to hand-held surgical lavage devices and methods for cleaning of the exposed tissues in surgeries such as prosthetic joint replacement, or repair of traumatic injury. The invention also relates generally to hand-held surgical delivery devices and methods, and more particularly, to surgical lavage/irrigation devices and methods for delivery of various therapeutic or bioactive agents to the surfaces and recesses of a surgical site such as bone prepared to receive a prosthetic implant.

BACKGROUND OF THE INVENTION

In the field of surgery, the importance of thorough cleaning of exposed tissues has long been recognized. In orthopedic surgery, the need for cleaning bony tissues is an added concern. Traumatic wounds, which can involve both soft and bony tissues, must be thoroughly cleansed of contaminants in order to minimize the risk of serious infection. The same risk requires that soft and bony tissues at surgical sites for procedures such as prosthetic joint replacement must also be thoroughly cleansed.

Cemented joint replacement surgery also requires especially thorough cleaning of the bone bed sculpted to receive an implant, for two additional reasons. The bone cement (typically polymethyl methacrylate) which secures the implant to the prepared bone is not an adhesive material, and accordingly, successful prosthetic fixation depends upon intimate mechanical interlock between cement and the open, three-dimensional network of cancellous bone surrounding the implant site. Thorough removal of fat, debris, and fluids from this bony network prevents these materials from forming an interposed layer between cement and bone, and thus allows for more direct cement-bone contact, helping to contribute to improved long-term mechanical fixation. Secondly, placement of cement into a prepared bony cavity, followed by insertion of the implant, often generates significant pressures which can force fat or particulate debris into the patient's circulatory system. Fat embolism has been a serious potential complication of cemented joint replacement surgery, but the incidence has been shown to be reduced by thorough cleaning, which removes substantial volumes of fat, marrow, and debris from the prepared bone bed.

Cleaning, or lavage, of the prepared bone surface or other tissue is generally accomplished by rinsing and flushing with a saline solution, which washes away surface debris. Traditionally, this has been accomplished by manually squirting saline from a bulb-style syringe. More recently, a variety of commercially available lavage devices have been developed, which deliver the saline solution in a pulsating stream, at higher flow rates and impact forces than can be readily achieved with manual delivery. Examples of these pulsatile lavage devices are described in U.S. Pat. No. 4,662,829 (Nehring), U.S. Pat. No. 4,583,531 (Mattchen), and U.S. Pat. No. 5,046,486 (Grulke et al.). Each of these devices delivers a stream of discrete pulses of saline to the surgical site.

Pulsatile lavage has been shown to contribute to improved cleaning of the trabecular bone. Intermittent flow may temporarily interrupt the formation of hydrostatic blockages in the bony pores, and further the pulses of saline may help the bone to "throw off" debris, as it rebounds from the impact of each delivered pulse. Mattchen and Grulke et al. both emphasize the importance of sharp irrigant pulses for effective cleaning. In both of these devices, the pulses of saline are delivered with relatively sharp on-off characteristics, so that the liquid stream comprises a series of repetitive impacts.

Each of the three devices mentioned above (Nehring, Mattchen, Grulke et al.) relies upon a pressurized gas to drive the pumping action. The gas typically employed is compressed nitrogen gas, which is readily available in the operating room because it is a common power source for surgical instruments such as drills and saws. The Nehring patent describes a diaphragm pump, in which the liquid is moved by the expansion of a flexible elastic diaphragm under pressure from the gas. Expansion of the diaphragm pressurizes the liquid contained in an adjacent chamber. Both the Mattchen and Grulke patents describe piston-style pumps to drive the saline solution. In each, the pump is powered by a compressed gas, as mentioned above. The Mattchen device employs a sliding valve timing assembly, and utilizes a disposable pump cartridge which is locked into position in a resterilizable handpiece for use. The Grulke device utilizes a spring-loaded piston pump, contained within a fully disposable handpiece unit to eliminate the need for hospital sterilization.

In all three of these devices, care is taken to ensure that the pathways for saline and pressurized gas are kept completely separate, and that the gas is safely vented away from the surgical site. This is an important patient safety feature, because the nitrogen gas typically employed with surgical instruments diffuses very slowly in physiological fluids, and therefore blood uptake of the gas can form a gas embolus, possibly leading to significant physiological disruption. Pressurized air directed at the surgical site could lead to similar problems, both because of its high nitrogen content and because oxygen also diffuses slowly in physiological fluids.

U.S. Pat. No. 5,037,437 (Matsen) describes a device for cleaning and drying the bone bed with a stream of physiologically benign flowing pressurized gas, to aid in more complete removal of debris and fluids. Flowing gas has been found to be helpful in loosening impacted bony debris and in lifting debris, fat and fluids from trabecular recesses and bringing them to the surface for more complete removal, which allows for better cement-bone interdigitation. This patent teaches the use of carbon dioxide or another gas with similar diffusibility in physiological fluids, an important safety feature to minimize any risk of gas embolism, as noted above.

Surgical procedures for repair of a variety of conditions caused by disease or traumatic injury may involve the application at the surgical site of one or more agents which serve therapeutic purposes. An example of this would be the application of antibiotics to the tissues exposed by the surgical or traumatic wound, to minimize the risks of wound infection and its accompanying physiological complications.

Surgical lavage devices are generally used to irrigate and cleanse the wound with saline solutions, and antibiotics may be added to the liquid solutions so that they can be washed over the surgical site. Other therapeutic or bioactive agents are applied topically to the exposed tissues. One example of this would be the use of topical hemostatic agents, often applied to the exposed bone surfaces to reduce bone bleeding in orthopedic joint replacement procedures. An agent such as thrombin or epinephrine is mixed into a small amount of liquid and dabbed onto the bone with surgical gauze sponges. In other instances, materials such as hydroxyapatite compounds are applied to the sculpted bone bed in order to facilitate bone growth and repair.

In contemporary surgical devices, delivery mechanisms for such materials are limited to admixing with volumes of saline, or manual delivery such as with sponges. In the first instance, the materials applied are diluted by the liquid solution, and are flushed through and across the site in the liquid stream, limiting the user's ability to place the material at a specific site. In the second instance, delivery efficiency is limited to the uppermost exposed surfaces which can be contacted by a sponge or similar device.

There is a need in the art for surgical devices and methods which address at least some of the above concerns or other concerns for preparing bone and other tissues.

SUMMARY OF THE INVENTION

The present invention enhances the efficiency of pulsatile saline or other liquid lavage by increasing the impact force which each saline pulse delivers. Increased saline impact force and momentum help to dislodge impacted debris, marrow and fat from the bone bed. This enhancement of saline lavage is accomplished by combining pulsed saline flow with pulses of a physiologically benign pressurized gas, such as carbon dioxide, in a hand-held lavage device. The device offers increased impact and cleaning efficiency via the rapidly alternating flow of saline and gas. The same pressurized gas is used as a power source for the saline pump mechanism. The gas utilized to drive each stroke of the pump mechanism is not vented away from the site, but is instead recirculated to the downstream end of the device, just upstream of the delivery nozzle. Each pulse of saline delivered by the pump mechanism is therefore immediately followed by a pulse of pressurized gas, which serves to further accelerate the saline pulse outward through the delivery nozzle. Thus, the resulting lavage stream does not merely include repetitive pulses of saline, but instead includes alternate pulses of saline and pressurized gas. The saline impact force is significantly increased (as much as 100%) over that delivered by the saline pumping mechanism alone. The alternate gas pulses also aid in loosening debris and preventing pooling of liquid in the trabecular recesses. The present invention also provides a gas bypass line to bypass the pump mechanism for gas-only delivery. The present invention also provides for liquid-only delivery, where the gas is vented to the atmosphere.

In one preferred embodiment, a surgical handpiece for effecting lavage is configured to accept a sterile disposable pump portion, and further incorporates a valve arrangement enabling the user to switch between the enhanced saline/gas combination lavage and straight gas lavage, so that final cleaning and drying of the implant site can be accomplished with flowing gas alone. Such an embodiment might also include a further valve setting, to allow the user to select a low-impact saline-only lavage, for use on soft tissues and other areas where irrigation is a more significant need than debridement and cleaning. Adjustment of this valve setting could allow for variability in lavage impact force, by varying the amount of gas which is vented and/or recirculated. In the preferred embodiment, a gas such as carbon dioxide, with a high diffusion coefficient in physiological fluids, would be employed.

The present invention is useable in a variety of surgical procedures including bone preparation for prosthetic implant, and cleansing and debridement of tissues comprised by trauma.

The present invention also delivers any of a variety of therapeutic or bioactive agents to a specific surgical site with a flowing gas stream. Preferably, the agents are delivered by utilizing the flowing pressurized gas stream used for final bony lavage as a delivery carrier. User convenience is enhanced by adding this delivery means to a hand-held surgical lavage device which delivers liquid and gas lavage from a single handpiece.

In one preferred embodiment, a surgical handpiece for effecting lavage incorporates a valve arrangement enabling the user to switch between liquid lavage and gas lavage. The gas lavage setting accommodates the addition of a reservoir of the desired additive agent which provides for introduction and dispersion of the agent into the flowing gas stream at the user's discretion. The handpiece of this embodiment allows the user to perform all surgical irrigation/lavage/delivery functions with a single self-contained unit. The present invention therefore is usable in a wide variety of surgical procedures, including most especially orthopedic procedures involving the preparation of bony tissues for repair or receipt of orthopedic devices such as prosthetic joint replacements.

BRIEF DESCRIPTION OF THE DRAWINGS

Throughout the following views, reference numerals will be used on the drawings, and the same reference numerals will be used throughout the several views and in the description to indicate same or like parts of the invention.

DETAILED DESCRIPTION OF THE INVENTION

The present invention provides for devices and methods for preparing bone/other tissue surfaces for prosthetic implantation and other surgical procedures by the application of liquid and/or gas. Preferably, the liquid is saline or other cleansing or therapeutic liquid pumped in short bursts to a bone/other tissue surface during surgery. Preferably, the gas is carbon dioxide ($CO_2$), or other physiologically benign pressurized gas. The liquid is preferably directed at the bone/other tissue surface in bursts of short duration. The gas is utilized to drive the pump mechanism, wherein the exhaust gas is either vented to the atmosphere or redirected at the bone/other tissue surface in combination with the liquid for increased surface cleansing or treatment of the bone/other tissue. Interim settings, in which a portion of the exhaust gas is vented while the remainder is redirected to the bone/tissue surface, are also possible in this embodiment. Alternatively, the gas bypasses the pump mechanism and is directed onto the bone/other tissue surface for further cleaning and localized drying of the bone bed. An additive agent reservoir may be added to the gas bypass line.

Figure 1:
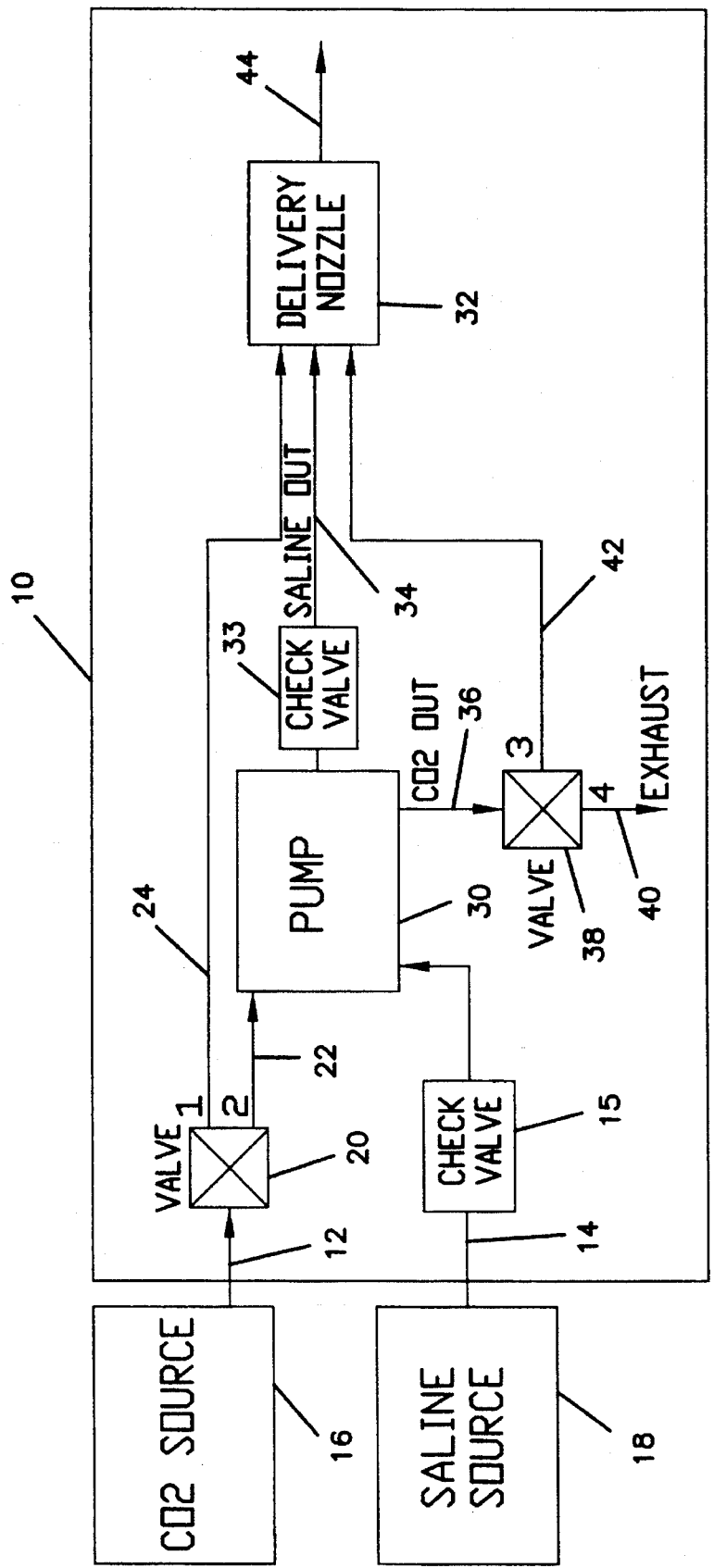
FIG. 1 is a schematic diagram of a lavage device in accordance with the invention.
Figure 2:
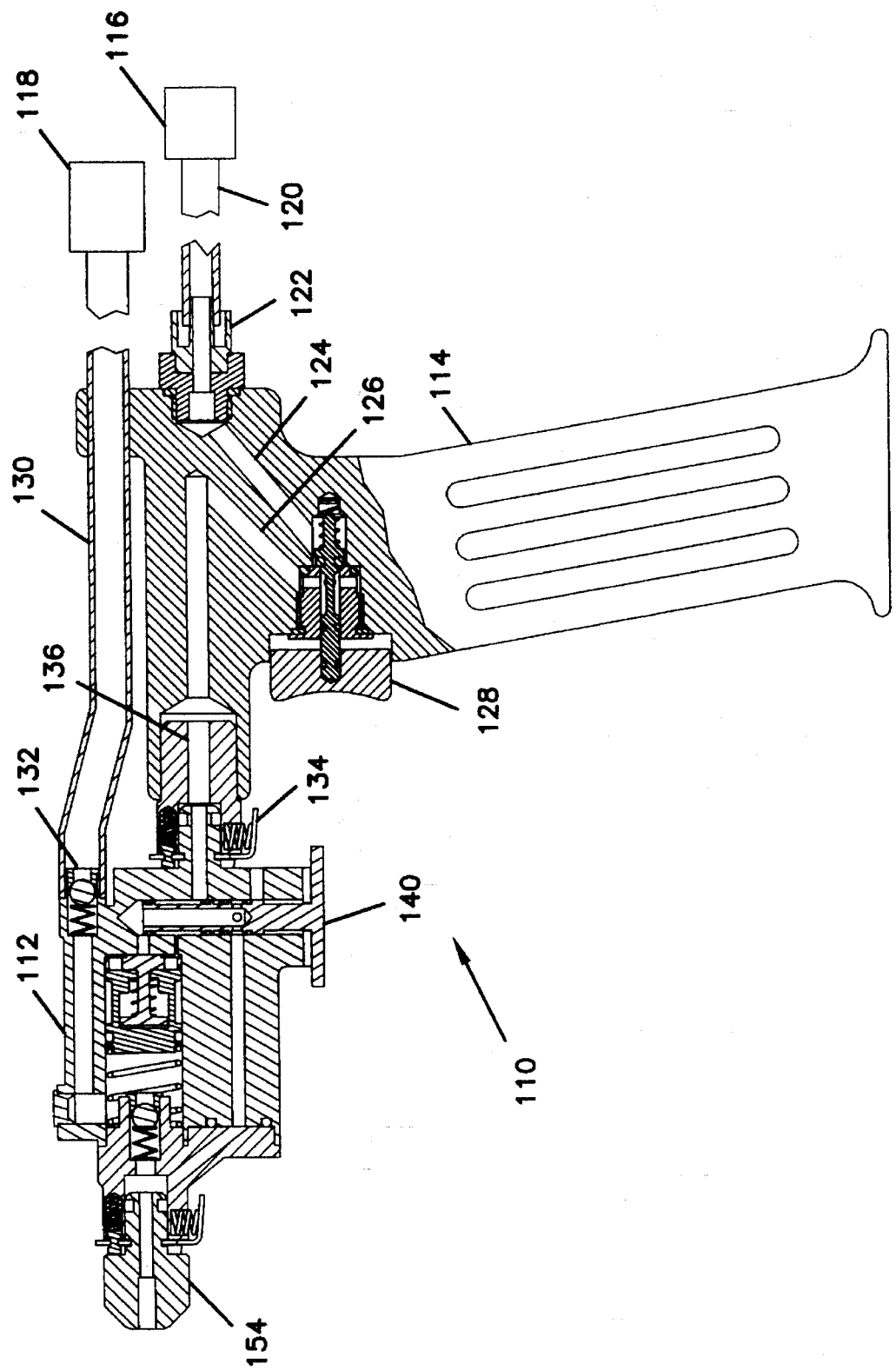
FIG. 2 is a cross-sectional view of one preferred embodiment of a lavage device in accordance with the present invention.

Referring now to FIG. 1, a schematic of a lavage device 10 is shown in accordance with the invention. A gas inlet line 12, and a liquid inlet line 14 provide inlet passages for the gas and the liquid, respectively, for use with lavage device 10. Gas source 16, preferably carbon dioxide, is supplied to gas inlet line 12 at a pressure above atmospheric pressure, such as 50 or 75 psi for example. Liquid source 18, preferably saline or other liquid, is supplied to liquid inlet line 14.

In the preferred embodiment, an inlet valve, or first valve 20, is interconnected to gas inlet line 12. A pump gas inlet line 22 connects first valve 20 to a gas driven reciprocating pump mechanism 30. It is to be appreciated that first valve 20 is optional in that gas inlet line 12 could be connected directly from gas source 16 to pump mechanism 30. First valve 20 could be either a linear or rotary style valve. In the preferred embodiment including first valve 20, a gas bypass line 24 runs from first valve 20 and bypasses pump mechanism 30 and connects to a nozzle 32 directly. As shown by FIG. 1, gas source 16 through appropriate control of first valve 20 is utilized to either operate pump mechanism 30 or to be applied directly to the bone surface at nozzle 32 in a controllable stream.

Pump mechanism 30 is a reciprocally driven pump mechanism, such as a diaphragm pump, or a piston pump, driven by pressurized gas. Pump mechanism 30 pumps liquid supplied from liquid source 18 through liquid inlet line 14 and a suitable check valve 15 to a liquid outlet line 34 connecting pump mechanism 30 to nozzle 32 through a suitable check valve 33. Check valves 15 and 33 maintain proper directional control of the liquid being pumped and prevent possible contaminating backflow.

Exhaust gas from pump mechanism 30 exhausts from pump mechanism 30 at a pump gas outlet line 36. An outlet valve, or second valve 38, directs exhaust gas from pump gas outlet line 36 to either an exhaust port 40 or a gas return line 42 from second valve 38 to nozzle 32. An interim setting is also possible, which directs gas to both ports simultaneously. When second valve 38 directs exhaust gas to gas return line 42, enhanced delivery of liquid from nozzle 32 is provided. Because of the reciprocating action of pump mechanism 30, the exhaust gas is released into gas outlet line 36 at the completion of the liquid pumping stroke which drives the liquid pulse into delivery nozzle 32. The gas pulse enters delivery nozzle 32 immediately behind the liquid pulse and imparts additional momentum to it. Alternating pulses of liquid and gas are thereby delivered through nozzle outlet 44 to the bone/other tissue surface. Second valve 38 could be either a linear or rotary style valve.

If enhanced output of the liquid from nozzle 32 is not desired, second valve 38 is operated to direct exhaust gas to exhaust port 40 instead of to gas return line 42. It is to be appreciated that second valve 38 is optional in that pump gas outlet line 36 could be connected directly from pump mechanism 30 to nozzle 32. However, as shown by the preferred embodiment of FIG. 1, gas source 16 is utilized to operate pump mechanism 30 and then, through appropriate control of second valve 38, either vented to the atmosphere or directed, fully or in part, to the inlet end of nozzle 32 to enhance delivery of the liquid pulses.

Preferred lavage device 10 is therefore operable in several modes. A first general mode of operation involves pumping liquid onto the bone/other tissue surface through nozzle 32 by pump mechanism 30. Within this mode of operation, at least two variations are possible. A first variation includes accelerated pulsing of the liquid by operating valve 38 to direct exhaust gas into gas return line 42 to nozzle 32. Such manner of operation (gas and liquid) is useful in initial cleaning/treating of the bone surface or other tissue.

A second variation of operation is a soft pulsing (liquid-only) mode where second valve 38 directs exhaust gas to exhaust port 40 instead of to nozzle 32. The liquid exits nozzle 32 under the influence of pump mechanism 30 only. Such manner of operation is useful in cleaning/treating or conventional bathing/irrigation of softer tissue.

A third optional variation of operation is a partially accelerated pulsing mode, in which a portion of the exhaust gas is vented, while the remainder is directed into gas return line 42 to nozzle 32. This interim setting may be particularly useful for cleaning traumatic wounds or bone stock which is weakened by disease processes. The relative amounts of gas vented to the atmosphere and delivered to the nozzle could be varied depending on the positioning of valve 38, if valve 38 is a variable position valve between the full accelerated pulsing of the liquid and gas, and the soft pulsing of liquid only settings.

A second general mode of operation involves operating first valve 20 to bypass pump mechanism 30 and direct gas through gas bypass line 24 directly to nozzle 32 for application to the bone surface or tissue. Such mode of operation is useful in a final step for cleaning and drying bone surfaces and/or removing loose debris.

Optionally, check valves may be provided in gas inlet line 12, pump gas inlet line 22, gas bypass line 24, pump gas outlet line 36, and gas return line 42 to maintain proper directional control of the gas flow.

In testing of the flow characteristics of the enhanced liquid flow vs. liquid only flow, it has been found that the impact force developed in the enhanced liquid flow of the full accelerated pulsing mode is twice as great as the liquid only flow of the soft pulsing mode.

One potential benefit of this enhanced saline lavage system is that more efficient cleaning can save operative time. If debris is removed more quickly and efficiently, cleaning can be accomplished with a lesser volume of liquid, and less liquid used also equates to less time needed for drying. Reduced volumes of liquid can also potentially reduce the magnitude of risk of cross-contamination of operating room personnel exposed to blood-borne pathogens when irrigating liquid and debris are splashed from the surgical site.

An additional benefit to this design as described here is the obviation of an additional power source for separately lavaging and drying the bone bed. Currently, the saline is pumped using either air or nitrogen-powered pumps, as described above in the prior art, or using electrical pumps. A separate source of carbon dioxide is then required for a final cleaning and drying technique with pressurized gas as in Matsen, for example. In the present invention, the carbon dioxide source provides both power for the liquid pump and pressurized gas for cleaning purposes. In the preferred embodiment, both saline and pressurized gas can be provided through a single combination handpiece, or handle portion, and nozzle assembly, or pump portion, with removable nozzle. The pump portion may be provided as a presterilized component; the separate handle portion and interchangeable nozzles can be disposable or resterilizable.

Referring now to FIGS. 2–10, one preferred embodiment of a lavage device 110 is shown. Lavage device 110 includes a pump portion 112, and a handle portion 114 which is separable from pump portion 112 at a latch 134. Such construction permits disposability of pump portion 112 and reuse of handle portion 114.

A gas source 116 interconnects via a conduit 120 to lavage device 110 at an inlet 122. A first gas line 124 and a second gas line 126 link inlet 122 to pump portion 112. A trigger arrangement 128 provides operator control of the gas flow from gas source 116 to pump portion 112.

A liquid line 130 links liquid source 118 to pump portion 112 of lavage device 110. A check valve 132 provides appropriate directional flow control over liquid entering pump portion 112.

Figure 3:
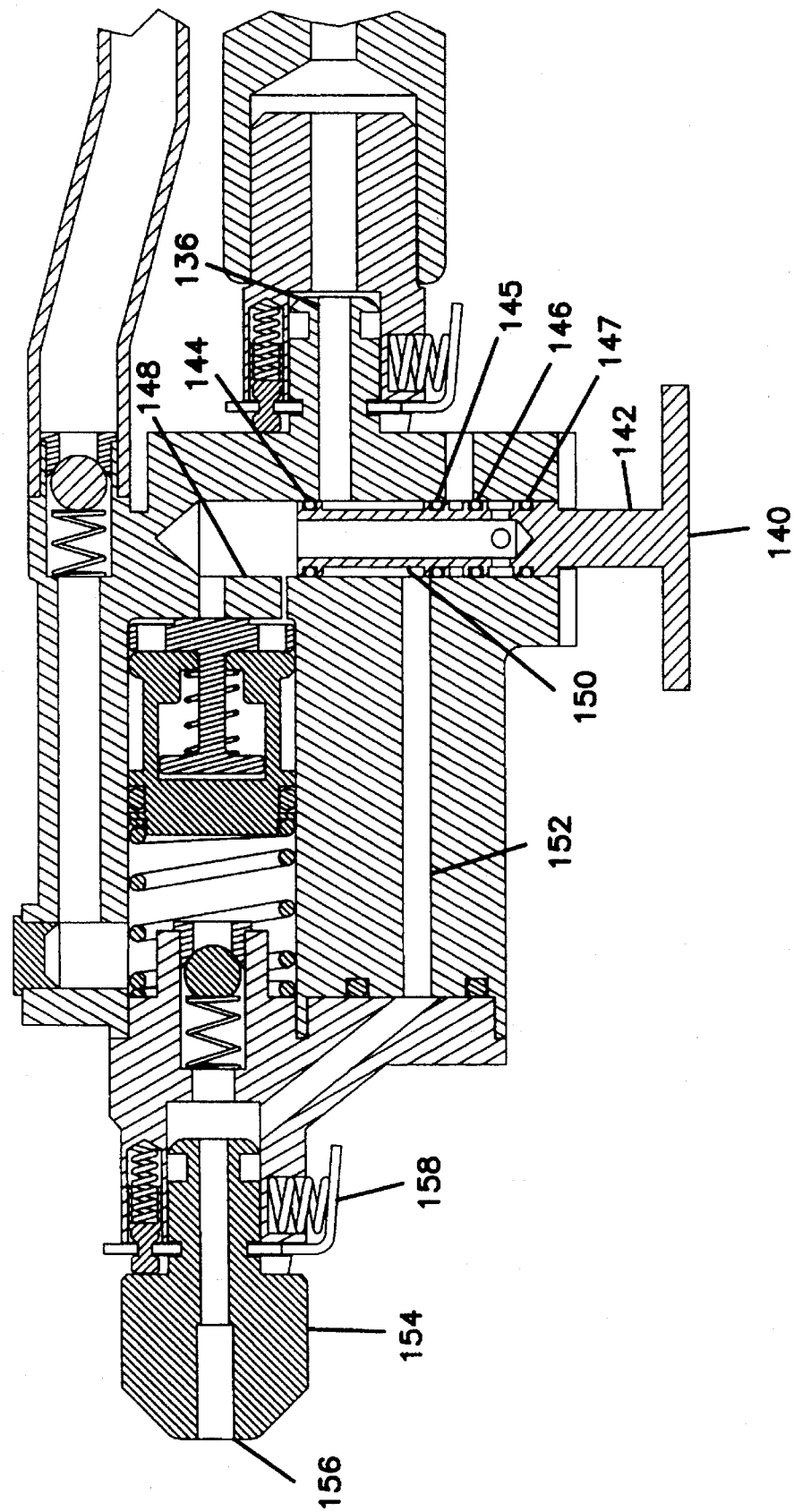
FIG. 3 is an enlarged cross-sectional view of the pump portion of the lavage device of FIG. 2 showing the device in the gas-only mode of operation.

The gas enters pump portion 112 at a first passage 136. A valve 140 is operatively positioned to direct gas flow from first passage 136 to one or more of three locations in the preferred embodiment. In a first mode of operation as shown in FIG. 3, gas flow is directed from first passage 136 to a gas bypass line 152 which leads to a nozzle 154 to exit lavage device 110 at a nozzle opening 156. Nozzle 154 is one example of a nozzle structure mounted to pump portion 112 with a latch arrangement 158. Other nozzles are possible depending on the desired flow characteristics, direction of flow, and location of a nozzle outlet 156 desired by the operator.

Valve 140 includes a stem 142 positioned in chamber 148. A plurality of peripheral seals 144, 145, 146, 147 are provided on stem 142 to seal against various portions of chamber 148. Stem 142 includes a recessed region 150 which interconnects first passage 136 to gas bypass line 152 in the gas-only mode of operation shown in FIG. 3.

Figure 4:
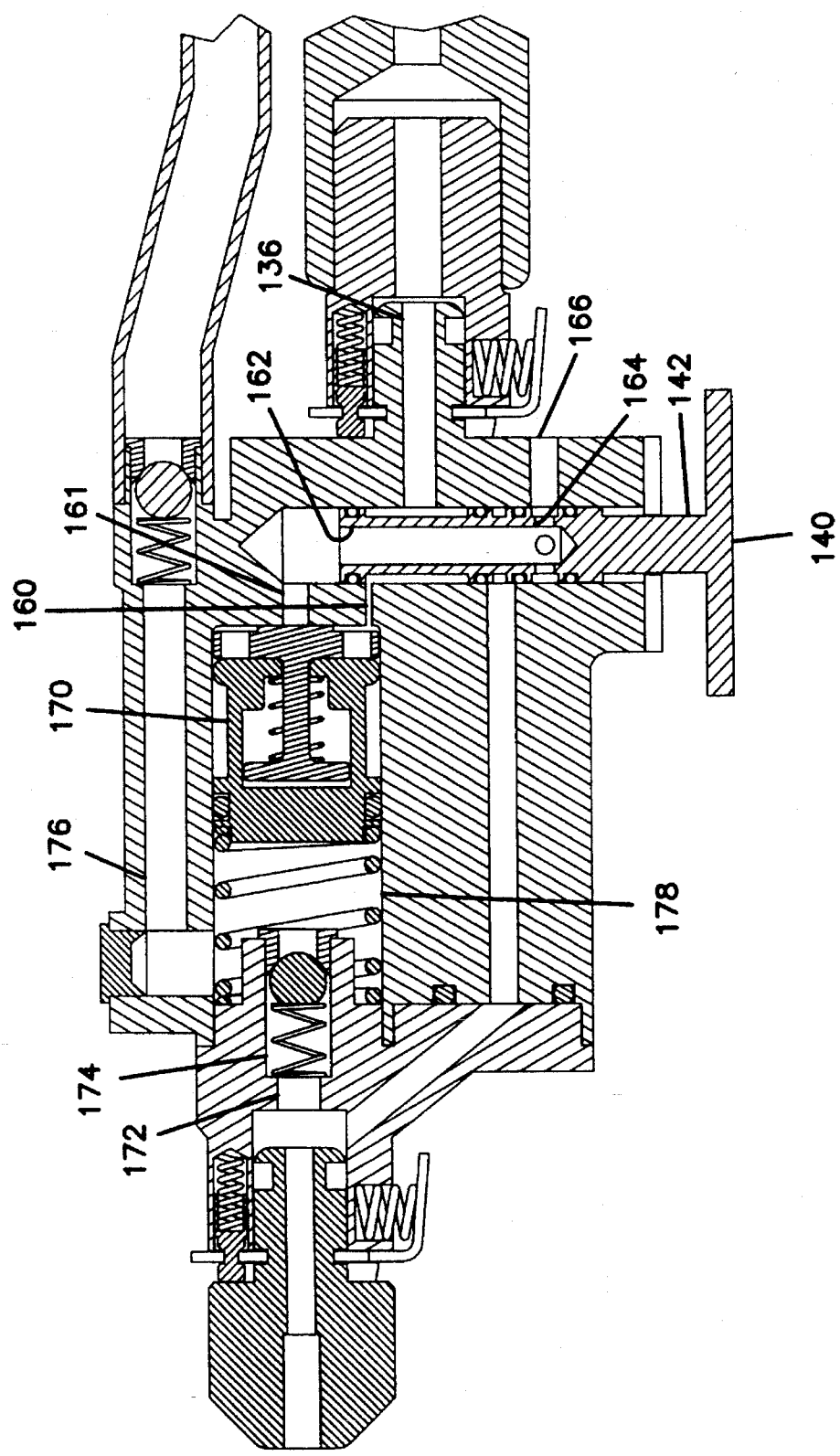
FIG. 4 shows the pump portion in the soft pulsing (liquid-only) mode of operation.

Referring now to FIG. 4, valve 140 is shown in a second mode of operation, the liquid-only soft pulsing mode. Valve 140 directs gas flow from first passage 136 to a pump inlet passage 160 for operation of a plunger arrangement 170 to pump liquid. The gas exhausts through a pump exhaust passage 161 through an interior passage 162 of stem 142 of valve 140 to a side outlet 164 which permits the gas to be exhausted from pump portion 112 at an exhaust port 166 to the atmosphere. The direction of exhaust port 166 can be varied so as to not exhaust onto the patient or the operator. Tubing can also be attached to this port to direct the exhaust gas away from the operative field. The gas entering pump inlet passage 160 provides reciprocating motion of plunger arrangement 170 to pump liquid from a liquid inlet 176 to a chamber 178 to a pump outlet 172. A check valve 174 provides directional flow control of the liquid from plunger arrangement 170.

Figure 5:
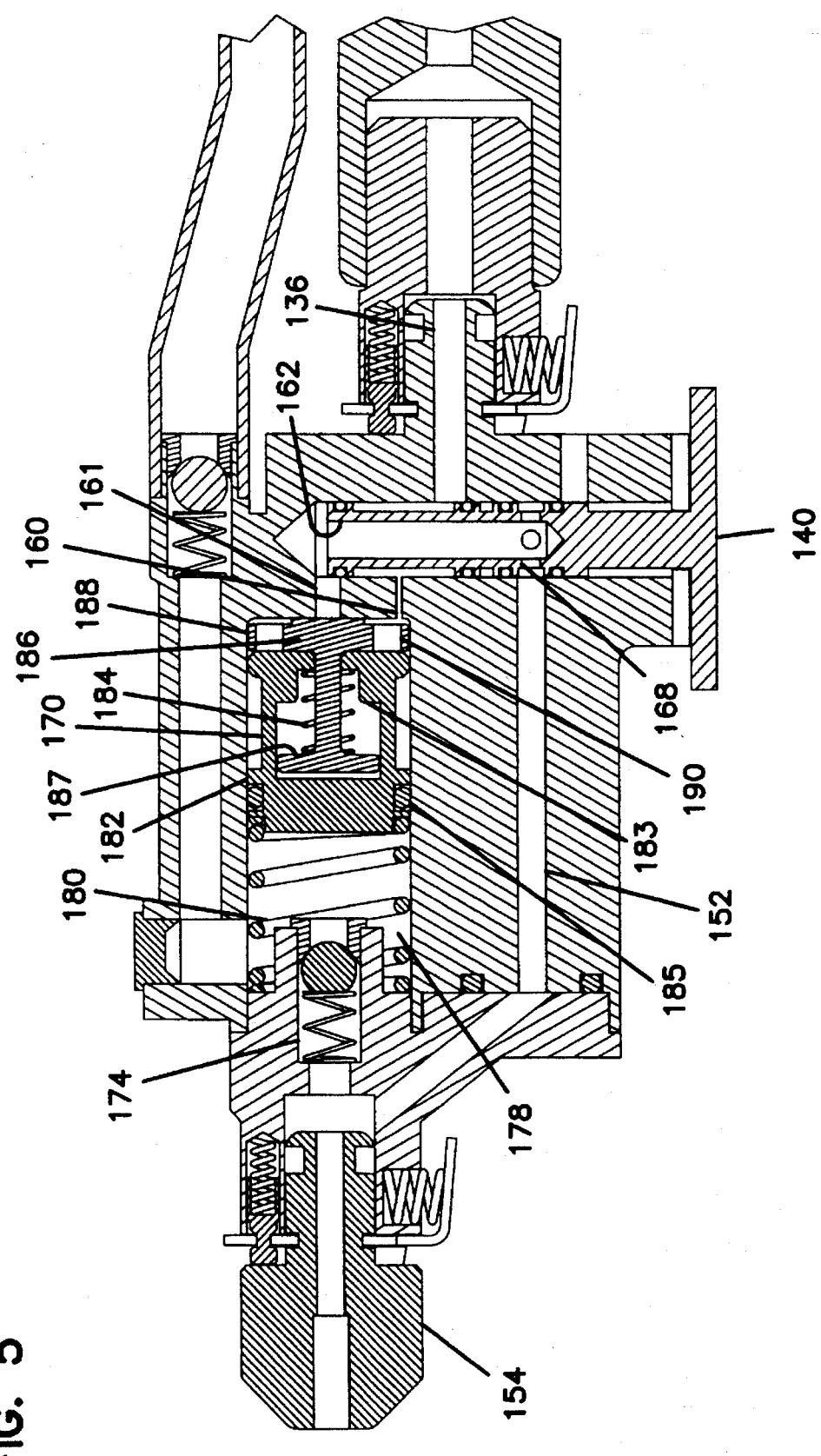
FIG. 5 shows the pump portion in the accelerated pulsing (gas and liquid) mode of operation during the filling phase.

Referring now to FIG. 5, valve 140 is in a third mode of operation, the accelerated pulsing mode. Gas from first passage 136 is directed to pump inlet passage 160 to operate plunger arrangement 170. Exhaust gas exits at pump exhaust passage 161 entering interior passage 162 and exiting at a side passage 168 to gas line 152 which directs the gas behind the pumped liquid at nozzle 154 to provide the accelerated pulsed liquid.

Valve 140 can be two separate valves if desired. In that case, each valve would need at least two positions. One valve would control gas inlet flow, and the other would control gas outlet flow.

Referring now to FIG. 5–9, operation of the plunger arrangement 170 will be described in greater detail. With respect to FIGS. 5–7, valve 140 is shown in the accelerated pulse mode of operation. Plunger arrangement 170 operates in a similar manner in both the accelerated pulsing mode of operation shown in FIGS. 5–7, and the soft pulsing mode of FIG. 4. As shown in FIG. 5, plunger arrangement 170 includes a large spring 180 which biases a first plunger portion 182 to a spaced apart distance from check valve 174. A large seal 185 seals the liquid from the gas. A second plunger portion 186 is mounted to first plunger portion 182 for reciprocating movement. A small spring 184 biases second plunger portion 186 to the position shown in FIGS. 5 and 7 relative to first plunger portion 182.

Figure 6:
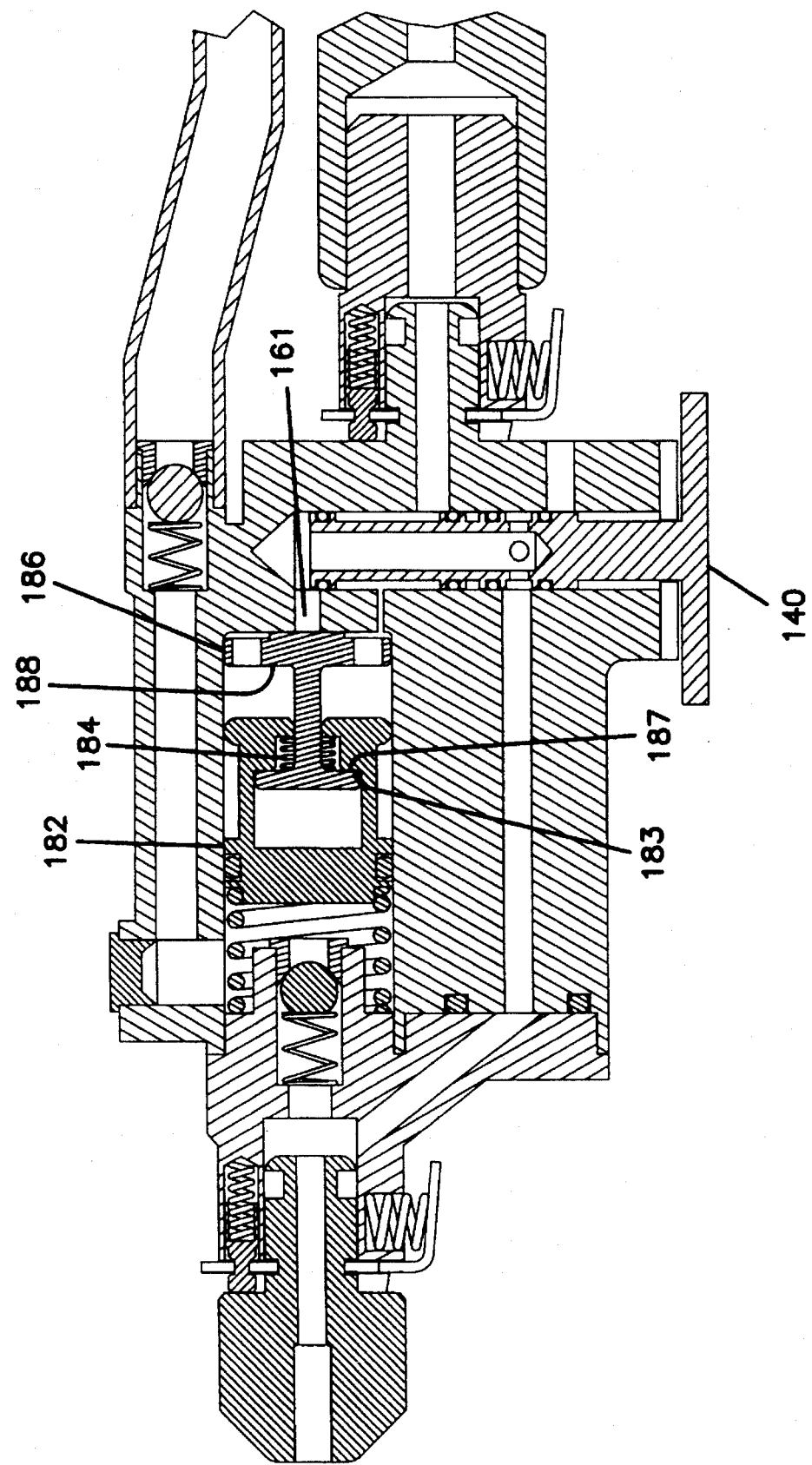
FIG. 6 shows the pump portion in the accelerated pulsing mode of operation during the pulse delivery phase.
Figure 7:
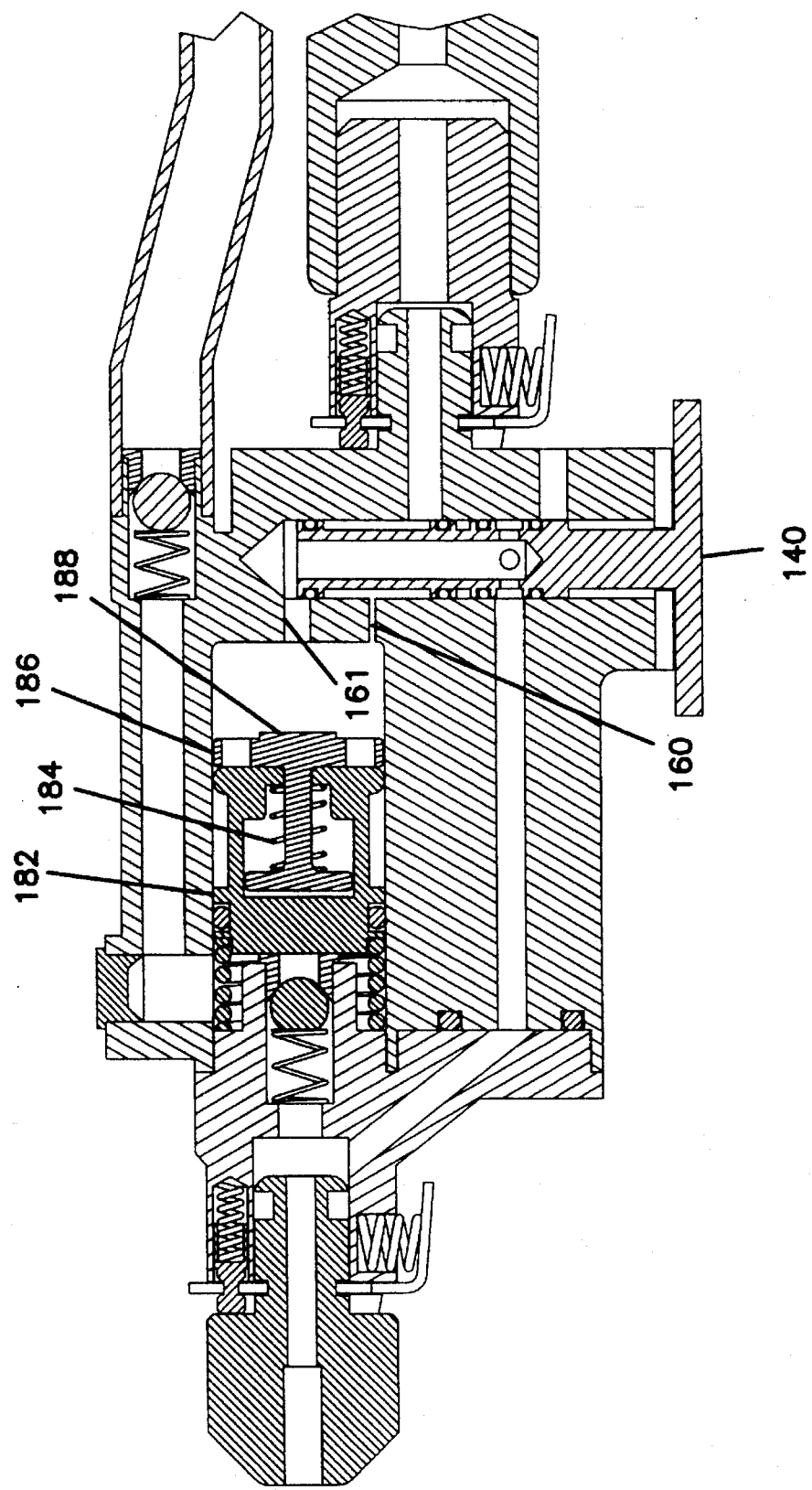
FIG. 7 shows the pump portion in the accelerated pulsing mode of operation at the end of the pulse delivery phase.

Peripheral holes 190 in a disc 188 of second plunger portion 186 are provided to allow gas entering at pump inlet passage 160 to push first plunger portion 182 against spring 180 toward check valve 174 to pump liquid in chamber 178. As first plunger portion 182 moves toward check valve 174, the gas will act to separate first plunger portion 182 from second plunger portion 186 against the spring force supplied by small spring 184 as shown in FIG. 6. Mechanical contact occurring between the internal shoulder 183 of first plunger portion 182 and the flanged portion 187 of second plunger portion 186 will begin to draw disc 188 away from exhaust passage 161, as shown in FIG. 6. As the gas begins to exhaust, small spring 184 rapidly draws second plunger portion 186 toward first plunger portion 182 as shown in FIG. 7. Pump exhaust passage 161 is large relative to pump inlet passage 160, allowing the gas to exhaust quickly at the end of each cycle.

Figure 8:
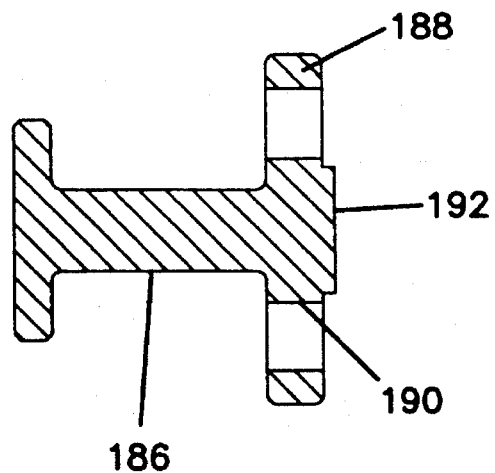
FIG. 8 is an enlarged cross-sectional view of the second plunger portion of the plunger arrangement of the pump mechanism.
Figure 9:
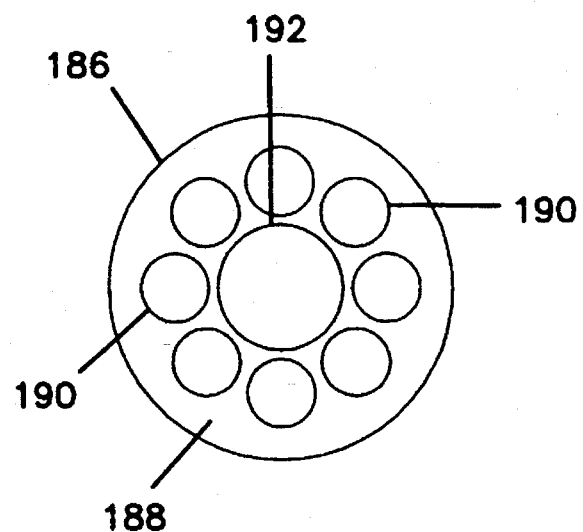
FIG. 9 is an end view of the second plunger portion of the plunger arrangement of the pump mechanism.

As shown in FIGS. 8 and 9, disc 188 of second plunger portion 186 includes a central gas stopper portion 192. Central gas stopper portion 192, when pulled away from pump exhaust passage 161, allows the gas to rapidly exhaust from the pumping chamber 178, which in turn allows large spring 180 to move first plunger portion 182 and second plunger portion 186 as a unit back to the position of FIG. 5 to close pump exhaust passage 161. Return of the plungers to their original position draws liquid into chamber 178 for the next pulse. In this manner, the pulses of liquid are pumped by plunger arrangement 170.

Figure 10:
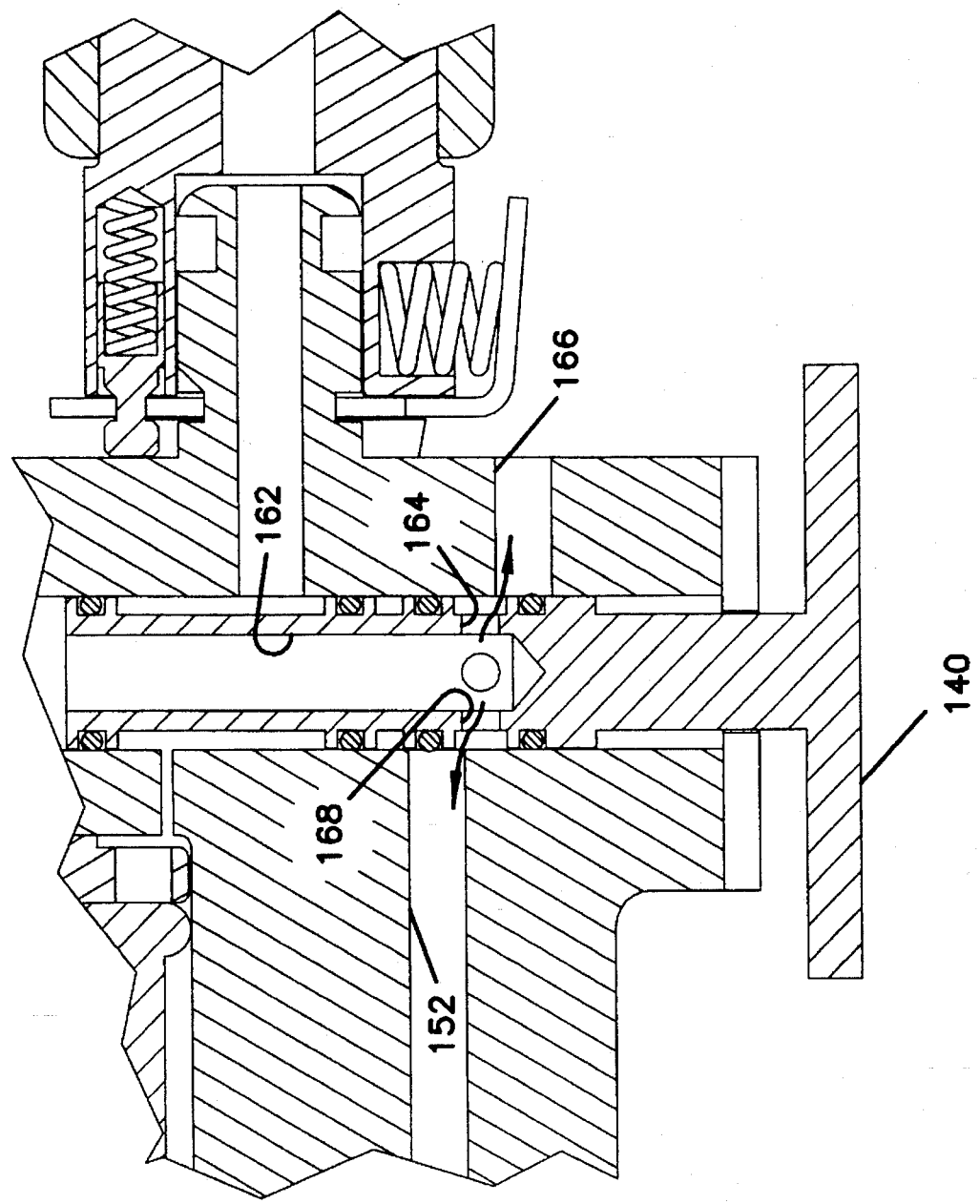
FIG. 10 shows the pump portion in a further enlarged view in an interim setting in which a portion of the exhaust gas is vented, and a portion is redirected to the bone/other tissue surface.

Referring now to FIG. 10, valve 140 is shown in an interim setting between the soft liquid-only pulsing mode and the accelerated pulsing mode. In the interim setting, exhaust gas enters interior passage 162. A portion of the exhaust gas exits at side passage 168 to gas line 152 which directs the gas behind the pumped liquid at nozzle 154 to provide a partially accelerated pulsed liquid. The remaining portion of the exhaust gas passes from interior passage 162 to side outlet 164 which permits the gas to be exhausted at exhaust port 166 to the atmosphere. The relative amounts of exhaust gas exiting at exhaust port 166 or entering gas line 152, respectively, can be varied in the preferred embodiment, depending on the position of valve 140.

The present invention also provides for devices and methods for surgical delivery of various therapeutic or bioactive additive agents separately from or in conjunction with surgical lavage and irrigation for cleansing and preparation of bony sites or surrounding soft tissues, in surgical and traumatic wounds. Preferably, the irrigating liquid is saline solution or other liquid cleansing agent, pumped in a pulsatile stream to bone/other tissue surface during surgery. Preferably, lavage is performed with this liquid in conjunction with carbon dioxide ($CO_2$), or other physiologically benign pressurized gas. The gas is utilized to drive the pump mechanism, and is further utilized to control various modes of liquid delivery. Alternatively, the gas bypasses the pump mechanism and is directed onto the bone/other tissue surface for further cleaning and localized drying of the prepared bone bed. In a further utilization, the flowing dry gas stream is utilized as a carrier to facilitate localized delivery of a variety of additive agents.

Figure 11:
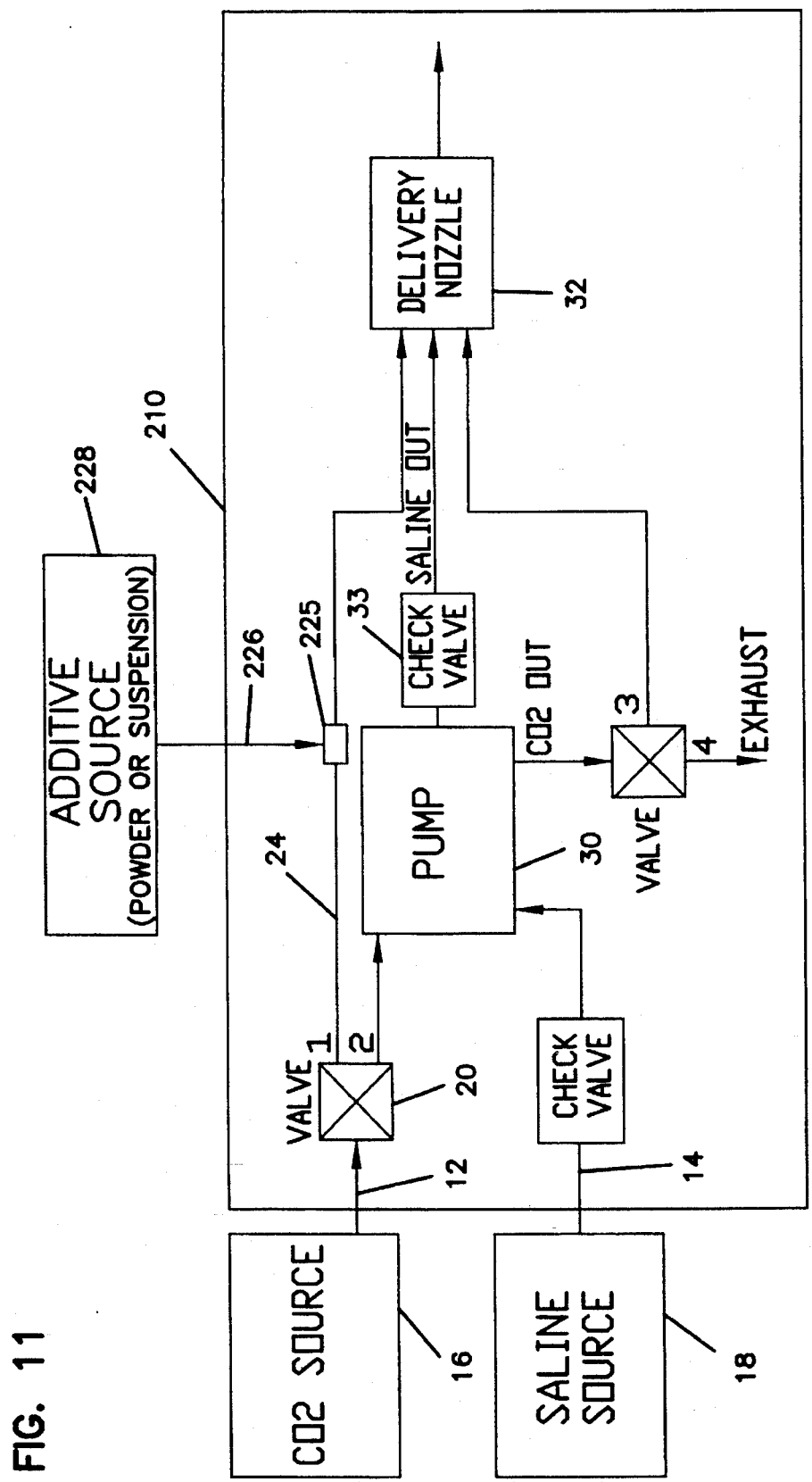
FIG. 11 is a schematic diagram of a lavage device like that shown in FIG. 1, and including a reservoir of a desired additive agent.

Referring now to FIG. 11, a schematic of a lavage device 210 is shown in accordance with the invention. Lavage device 210 is similar to lavage device 10 shown in FIG. 1. A gas inlet line 12, a liquid inlet line 14, and an additive inlet line 226 provide inlet passages for the gas, liquid, and additive agents, respectively, for use with lavage device 210. Gas source 16, preferably carbon dioxide, is supplied to gas inlet line 12 at a pressure above atmospheric pressure, such as 50 or 75 psi, for example. Liquid source 18, preferably saline or other liquid, is supplied to liquid inlet line 14. Additive source 228, in a powder or suspension form, is optionally supplied to additive inlet line 226.

Lavage device 210 is useable in a similar manner as lavage device 10 with respect to the mode of operation allowing delivery of liquid. In the second general mode of operation, first valve 20 is operated to bypass pump mechanism 30 and direct gas through gas bypass line 24 directly to nozzle 32 for application to the bone surface or tissue. Within this mode of operation, two variations are possible. An inlet port 225 for inlet of additive source 228 through additive inlet line 226 permits uptake of the additive agent by the flowing gas stream, and directs gas and additive together to nozzle 32 for delivery to the bone or tissue surface. This mode can be used whenever the operator desires delivery of the specific additive agent selected. Alternatively, additive inlet port 225 can be sealed so that the gas in gas bypass line 24 passes directly to nozzle 32. This mode of operation is useful as a final step for cleaning and drying the bone surface and/or removing loose debris. Optionally, a check valve may be provided in additive inlet line 226 to maintain proper directional flow control.

In the process of preparing a bone bed or other surgical site, device 210 would be utilized after the debris and fluids had been flushed away by liquid lavage and preliminary gas lavage. The additive agent could be delivered as a dry particulate in the flowing gas stream, or could be mixed in a small amount of liquid prior to surgical delivery. This liquid mixture could then be atomized and delivered as a fine mist or spray in conjunction with the flowing dry gas stream.

This delivery method could be utilized for placement of a therapeutic or bioactive material which the operator did not want diluted or flushed away by liquid delivery. Flowing gas travels through all the open interconnected recesses of the bony network surrounding the surgical site and can therefore ensure contact of the desired material with specific locations, deep and superficial. Materials which could be delivered in this fashion include antibiotics and similar antiseptic agents; hydroxyapatite or similar bioactive materials intended to promote bone healing and re-growth; topical and resorbable hemostatic agents, such as thrombin, epinephrine, adrenaline, microcrystalline collagen, gelatins, or oxidized cellulose, intended to control oozing blood from the bone, which can otherwise interfere with the cement-bone interface; and other chemical agents serving a purpose in healing or fixation, such as, for example, "primers" for future bone cement materials.

From the foregoing detailed description of the present invention, it has been shown how the objects of the invention have been obtained in a preferred manner. However, modifications and equivalents of the disclosed concepts, such as those which would readily occur to one skilled in the art, are intended to be included within the scope of the claims.

What is claimed is:

1. A method of preparing bone and other tissue comprising the steps of:
    a) supplying pressurized gas to a pump device having a gas-driven pump mechanism for pumping liquid and a nozzle interconnected to the pump mechanism;
    b) supplying liquid to be pumped to the pump device;
    c) reciprocally driving the pump mechanism of the pump device with the gas to pump the liquid to the nozzle of the pump device;
    d) directing exhaust gas from the pumping mechanism to the nozzle; and
    e) directing the nozzle at a tissue surface, wherein the liquid and the exhaust gas exit the nozzle.

2. The method of claim 1, after step e), further comprising the steps of:
    a) bypassing the pump mechanism with the gas;
    b) directing the gas to the nozzle; and
    c) directing the nozzle at the tissue surface, wherein only the gas exits the nozzle.

3. The method of claim 2, further comprising the step of adding an additive to the gas bypassing the pump mechanism wherein the gas and the additive exit the nozzle.

4. The method of claim 1, after step e), further comprising the steps of:
    a) directing the exhaust gas from the pump mechanism away from the nozzle and into the atmosphere; and
    b) directing the nozzle at the tissue surface, wherein only the liquid exits the nozzle.

5. The method of claim 4, after step b) of claim 4, further comprising the steps of:
    a) bypassing the pump mechanism with the gas;
    b) directing the gas to the nozzle; and
    c) directing the nozzle at the tissue surface, wherein only the gas exits the nozzle.

6. The method of claim 1, after step e), further comprising the steps of:
    a) directing a portion of the exhaust gas from the pump mechanism away from the nozzle and into the atmosphere; and
    b) directing the nozzle at the tissue surface, wherein the liquid and the remaining portion of the gas exit the nozzle.

* * * * *